(12) United States Patent
Oertling et al.

(10) Patent No.: US 7,846,886 B2
(45) Date of Patent: Dec. 7, 2010

(54) MIXTURES OF UNSATURATED MACROCYCLIC EPOXIDES AS ODORIFEROUS SUBSTANCES

(75) Inventors: Heiko Oertling, Holzminden (DE); Horst Surburg, Holzminden (DE)

(73) Assignee: SYMRISE GmbH & Co. KG, Holzminden (DE)

( * ) Notice: Subject to any disclaimer, the term of this patent is extended or adjusted under 35 U.S.C. 154(b) by 128 days.

(21) Appl. No.: 12/223,633

(22) PCT Filed: Jan. 10, 2007

(86) PCT No.: PCT/EP2007/050203

§ 371 (c)(1), (2), (4) Date: Oct. 23, 2008

(87) PCT Pub. No.: WO2007/090704

PCT Pub. Date: Aug. 16, 2007

(65) Prior Publication Data

US 2009/0305928 A1  Dec. 10, 2009

Related U.S. Application Data

(60) Provisional application No. 60/765,672, filed on Feb. 7, 2006.

(51) Int. Cl.
*C11D 3/50* (2006.01)

(52) U.S. Cl. ....................................... 510/104; 512/13

(58) Field of Classification Search .................. 510/104; 512/13

See application file for complete search history.

(56) References Cited

U.S. PATENT DOCUMENTS 3,681,395 A * 8/1972 Mookherjee et al. ........ 549/271
4,885,397 A * 12/1989 Bueschken ................... 568/341

FOREIGN PATENT DOCUMENTS

DE  2111753  10/1971
EP  322537  7/1989

OTHER PUBLICATIONS

Mookherjee, Braja D. et al: "Synthesis of .DELTA.9-isoambrettolide and its isomers from 1, 9-cyclohexadecadiene" Journal of Organic Chemistry, 37(24), 3846-8 Coden: Joceah; ISSN: 0022-3263, 1972, XP002051897.
Mookherjee, B. D. et al: "Synthesis of racemic muscone and cyclopentadecanone (exaltone) from 1, 9-cyclohexadecadiene" Journal of Organic Chemistry, 36(22), 3266-70 Coden; Joceah; ISSN: 0022-3263, 1971, XP002432756.

* cited by examiner

*Primary Examiner*—John R Hardee
(74) *Attorney, Agent, or Firm*—Connolly Bove Lodge & Hutz LLP

(57) ABSTRACT

A mixture of 17-oxabicyclo[14.1.0]heptadec-8-ene and its isomers as an odoriferous substance and an odoriferous or aroma substance mixture comprising 17-oxabicyclo[14.1.0]heptadec-8-ene and one or more further odoriferous or aroma substances are described.

19 Claims, No Drawings

MIXTURES OF UNSATURATED MACROCYCLIC EPOXIDES AS ODORIFEROUS SUBSTANCES

CROSS-REFERENCE TO RELATED APPLICATIONS

This application claims benefit of priority to PCT Publication No. WO2007090704, filed on Jan. 10, 2007, which asserts priority to U.S. Provisional Application No. 60/765,672, filed on Feb. 7, 2006, which are incorporated herein by reference in their entireties.

The present invention relates to the compound 17-oxabicyclo[14.1.0]heptadec-8-ene in a certain isomer composition as well as odoriferous substance and aroma substance mixtures of 17-oxabicyclo[14.1.0]heptadec-8-ene in a certain isomer composition and the respective use thereof as odoriferous or aroma substance mixtures, as well as corresponding perfumed products.

In the perfume industry there is generally a need for musk odoriferous substances, since new and modern fragrances having a musk fragrance are continuously to be made available to consumers. Because of the consumer's increasing demand for new, modern fragrance notes, in the perfume industry there is a constant need for fragrances with which novel effects can be achieved in perfumes and new fashion trends can be created in this manner.

Compounds having a musk smell have always been important and sought-after components in the fragrance industry. Musk odoriferous substances are thus nowadays employed in many perfume compositions.

Typical macrocyclic musk odoriferous substances are distinguished by a ring having 13 to 17 C atoms, which carries a ketone or an ester as a functional group. Conventional musk odoriferous substances are e.g. zibetone, muscone, cyclopentadecanolide, ethylene brassylate and cyclopentadecanone. Perfumers generally refer to a "macro-musk smell" of these musk substances, the individual compounds sometimes varying very significantly from one another in individual notes and aspects.

For creation of novel modern compositions, there is a constant need for musk odoriferous substances having particular olfactory properties which are suitable for serving as a basis for composition of novel, modern perfumes having a complex musk character. The musk odoriferous substances sought should have further notes and aspects, alongside the typical musk smell, which impart to them olfactory character and complexity.

The search for suitable musk odoriferous substances which led to the present invention was made difficult by the following circumstances:

The mechanisms of perception of smell are not adequately known.

The relationships between the specific perception of smell on the one hand and the chemical structure of the associated odoriferous substance on the other hand have not been adequately researched.

Slight changes in the structural make-up of a known odoriferous substance often already have the effect of marked changes in the sensorial properties and impair the tolerability for the human organism.

Success in the search for suitable musk odoriferous substances therefore depends greatly on the intuition of the searcher.

It was therefore the object of the present invention to discover macrocyclic musk compounds having novel olfactory properties, with which particular olfactory notes and aspects can be imparted to odoriferous substance compositions.

The object is achieved by mixtures according to claim 1. In this context, the expression that an isomer mixture contains only two or three isomers means that the particular total mixture or a product comprising the total mixture contains not more than the said two or three isomers, that is to say that one or two of the four isomers is/are not contained in the product or the total mixture.

It has been found that the two (E) double bond isomers (1) and (2), but in particular the (Z)-epoxide (1) of (E)-17-oxabicyclo[14.1.0]heptadec-8-ene, have an extremely intensive and perfumistically very sought-after natural musk smell which the other isomers do not share to this degree. The sensorial properties of mixtures of the two (E) isomers (1) and (2) prove to be likewise advantageous.

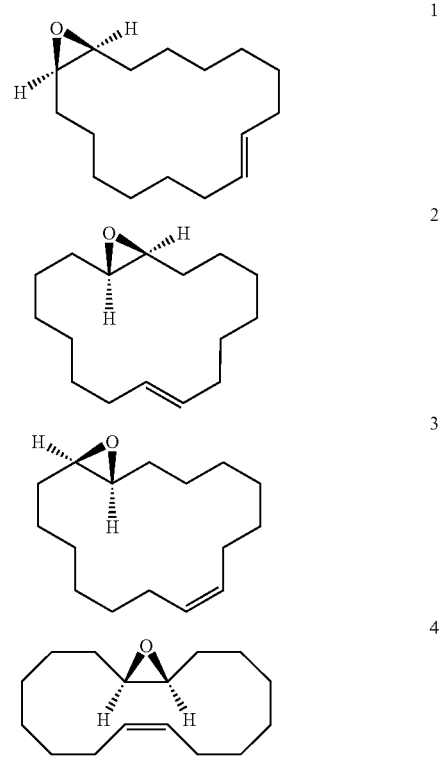

In the above structural formulae (1) to (4), in each case only one enantiomer of the particular compound is shown. The numbering of the structural formulae (1-4) relates to the racemic mixtures of the particular isomers.

Where 17-oxabicyclo[14.1.0]heptadec-8-ene is referred to in the following, this means a mixture containing the isomers (1), (2), (3) and (4), unless stated otherwise.

Where (E)-17-oxabicyclo[14.1.0]heptadec-8-ene is referred to in the following, this means the compounds (1) and (2) or mixtures containing these compounds, unless stated otherwise.

The synthesis of a mixture of the particular (E/Z) isomers of 17-oxabicyclo-[14.1.0]heptadec-8-ene has been described in J. Org. Chem. 1972, 3846 and J. Org. Chem. 1971, 3266, by epoxidation of 1,9-cyclohexadecadiene. Starting from an (E/Z) isomer mixture of 1,9-cyclohexadecadiene, all four isomers of 17-oxabicyclo[14.1.0]heptadec-8-ene are obtained. A "weak musk smell" is stated as the olfactory characterization of the compounds obtained in this way. Precise information on the isomer composition is lacking.

DE 2111753 claims the compound 17-oxabicyclo[14.1.0] heptadec-8-ene without stating the isomer composition. The individual sensorial value of the compound (1) was not described there.

Both the abovementioned publications and the patent mentioned last subscribe in the synthesis of its educt material, 1,9-cyclohexadecadiene (1,9-CHDD), to a process disclosed in J. Polym. Sci. 1967, 2209 or U.S. Pat. No. 3,439,056: Cyclooctene is dimerized to 1,9-cyclohexadecadiene with the aid of tungsten hexachloride and ethylaluminium dichloride. In the publications mentioned, no conclusions are drawn regarding the isomer composition of the 1,9-cyclohexadecadiene obtained in this way. If cyclooctene is dimerized in accordance with the method described, the following isomer distribution is obtained: 35 wt. % (Z,Z)-1,9-cyclohexadecadiene, 53% (Z,E)-1,9-cyclohexadecadiene and 12% (E,E)-1,9-cyclohexadecadiene.

DE 1793138 and U.S. Pat. No. 3,935,270 disclose the synthesis of 17-oxabicyclo[14.1.0]heptadec-8-ene by means of per-acid epoxidation of 1,9-cyclohexadecadiene. The isomer composition of the epoxides, on the other hand, and the specific olfactory value of individual isomers were not described, since these were used as intermediates for the synthesis of cyclohexadecenones.

The same applies to the patent family DE 3744094, EP 322537 or U.S. Pat. No. 4,885,397, in which the preparation of macrocyclic ketones by rearrangement from the corresponding epoxides is disclosed.

If an isomer mixture of 1,9-cyclohexadecadiene is epoxidized with various peracids in accordance with the prior art (in this context see U.S. Pat. No. 3,681,395, DE 2111753, U.S. Pat. No. 3,935,270, DE 1793138 or also J. Org. Chem. 1971, 3266), the double bonds in the (E/Z)-1,9-cyclohexadecadiene react at different speeds. The following conversion factors with per-acids result for the individual isomers: Compound (3) is formed with the factor 0.78, whereas compound (1) is formed with the factor 1.22 (see example). For the 1,9-CHDD isomer distribution obtained according to U.S. Pat. No. 3,439,056 or DE 1793138, this results in a product mixture of the following composition: 32% compound (1), 12% compound (2), 21% compound (3) and 35% compound (4) (all values in wt. %). Compound (4), which is of minor olfactory value, is therefore the main product of such an oxidation, and in DE 2111753, U.S. Pat. No. 3,935,270, DE 1793138 and J. Org. Chem. 1971, 3266 sensorially the most productive compound (1) is a constituent of the product mixture to the extent of only 32 percent. The (E) double bond content of the mixture obtained in this way, that is to say the total content of compounds (1) and (2) in the particular mixtures, was 44 percent.

In U.S. Pat. No. 4,822,874 und DE 3716181, (Z/E)-8-cyclohexadecenone (8-CHD) is used as a complexing agent in order to isolate cyclooctaamylose in a pure form. A corresponding synthesis of the material is described in Supramolecular Science 1998, 5, 101: Starting from a cyclohexadecadiene mixture having an (E) double bond content (total content of the (E) isomers (1) and (2) in the mixture) of 80%, after an epoxidation step and subsequent opening of the epoxide, 8-cyclohexadecenone is obtained with an (E) double bond content of 71.9% and a (Z) double bond content of 28.1%. No information is given either on the epoxidation process or on the isomerization of the epoxides to give the 8-cyclohexadecenone. Therefore, no conclusion can be drawn as to what composition existed in the isomer mixture of the epoxides.

Summarizing, it can be said that none of the epoxide mixtures synthesized to date contained more than 32 wt. % (E)-17-oxabicyclo[14.1.0]heptadec-8-ene (1). The olfactory quality of the compound (E)-17-oxabicyclo[14.1.0]heptadec-8-ene (1) has not hitherto been determined.

It has now been found, surprisingly, that 17-oxabicyclo[14.1.0]heptadec-8-ene of the formula (1) differs significantly in olfactory properties from its isomers. The descriptions of the smell of individual isomers and of the isomer mixtures of 17-oxabicyclo[14.1.0]heptadec-8-ene are given in Table 1.

TABLE 1

| | Compound/mixture | Smell description |
|---|---|---|
| A | (E)-17-Oxabicyclo-[14.1.0]heptadec-8-ene formula (1) | The isomers investigated in the following (B-D) and mixtures thereof all contrast greatly with pure (1): The musk smell thereof is animal, pure in tone, fine in quality and in the initial smell has the typical "dry-down" note of freshly ironed laundry, powdery and natural, additionally with a clear nitro-musk component. In the after-smell much more radiant musk body than for example (3); powdery and animal, very elegant. |
| B | (E)-17-Oxabicyclo-[14.1.0]heptadec-8-ene formula (2) | In the initial smell a strong, pure musk smell, pleasant nitro-musk note, with erogenous and slightly powdery radiance. Then increasingly more complex with a woody timbre. Significant macro-musk smell, warm, dry, nature-like and round, weakly apricot-like nuance. |
| C | (Z)-17-Oxabicyclo-[14.1.0]heptadec-8-ene formula (3) | Initially flat, but clean musk note, pleasant nitro-musk overtone, slightly woody aspect. Then highly levelling musk note with animal aspects. |
| D | (Z)-17-Oxabicyclo-[14.1.0]heptadec-8-ene formula (4) | In the initial smell a weak musk, dry, metallic aspect. Muffled. Thereafter not very radiant musk smell, somewhat erogenous, somewhat woody. |
| E | Mixture of (1) and (2) | Starting as an exalting, clear but nevertheless complex musk smell, then more significantly nitro-musk, crystalline, erogenously animal, round with woody aspects, warm, radiant and natural. Slightly flowery-sweet nuance. Sensorially very valuable. |
| F | Mixture of (1) and (3) | Initial smell: pure in tone, slightly woody and crystalline, scarcely erogenous, much less valuable than mixture E, zibetone-like, more quickly levelling, then nitro-musk with animal components. |

Mixtures E and F evaluated for their olfactory properties had the following composition (values according to GC analysis):

Mixture E, i.e. the mixture of compounds (1) and (2), contained, according to GC analysis, 61 wt. % of formula (1) and 35 wt. % of formula (2). The (E) double bond content was therefore 96 wt. %.

Mixture F, i.e. the mixture of compounds (1) and (3), contained, according to GC analysis, 23 wt. % of formula (1) and 70 wt. % of formula (3). The (E) double bond content of the mixture was therefore 23 wt. %.

(E)-17-Oxabicyclo[14.1.0]heptadec-8-ene (1) and (2) unexpectedly differ significantly in olfactory properties from (Z)-17-oxabicyclo[14.1.0]heptadec-8-enes (3) and (4), and the mixtures in particular by the valuable naturalness which is sought after perfumistically, coupled with the pleasant nitro-musk note. Of the compounds and mixtures investigated here, (E)-17-oxabicyclo[14.1.0]heptadec-8-ene (1) shows the strongest and most elegant musk smell, in particular a powdery nitro-musk note.

The mixture of compounds (1) and (2) has a more complex musk smell than the individual isomers (2); particularly intensified by a sought-after nitro-musk smell, to which is added a woody aspect. Preferred weight ratios of (1) to (2) are from 1:50 to 50:1, particularly preferably from 10:1 to 1:10.

Mixture E with a high (E) content, according to Table 1, has a considerably higher intensity, complexity and elegance compared with mixture F, which is enriched in (Z) isomers (see Table 1), and is therefore likewise suitable for use in novel and modern perfume compositions.

In mixtures with other odoriferous substances, the mixture according to the invention of (E)-17-oxabicyclo[14.1.0]heptadec-8-ene (1) with its isomers is already capable of increasing the intensity of an odoriferous substance mixture in low dosages and of rounding off the overall olfactory properties of the odoriferous substance mixtures, and of imparting to the mixture more radiance and naturalness. In higher dosages, the clean, powerful musk smell takes effect, accompanied by the pleasant nitro-musk note.

Summarizing, the following compounds and mixtures according to the invention therefore have a surprising olfactory quality:

(i) mixtures of 17-oxabicyclo[14.1.0]heptadec-8-ene isomers having a content of (E)-17-oxabicyclo[14.1.0]heptadec-8-ene (1) of at least 32 wt. %, preferably of at least 40 wt. % and particularly preferably of at least 50 wt. %, preferably those mixtures which contain all the isomers (1), (2), (3) and (4) here;

(ii) mixtures of 17-oxabicyclo[14.1.0]heptadec-8-ene according to (i), wherein the (E) double bond content, that is to say the content of isomers (1) and (2) in the total mixture, is simultaneously at least 45 wt. %, preferably at least 55 wt. % and particularly preferably at least 60 wt. %, again preferably those mixtures which contain all the isomers (1), (2), (3) and (4) here;

(iii) odoriferous or aroma substance mixtures comprising mixtures of (E)-17-oxabicyclo[14.1.0]heptadec-8-ene (1) corresponding to (i) or (ii) and one or more further odoriferous or aroma substances, in particular (iv) odoriferous or aroma substance mixtures comprising (E)-17-oxabicyclo[14.1.0]heptadec-8-ene (1) and (E)-17-oxabicyclo[14.1.0]heptadec-8-ene (2) and optionally one or more further odoriferous or aroma substances, wherein the weight ratio of (E)-17-oxabicyclo[14.1.0]heptadec-8-ene (1) to (E)-17-oxabicyclo[14.1.0]heptadec-8-ene (2) is preferably 10:1 to 1:30, particularly preferably 4:1 to 1:25.

The perfumistically valuable isomer compositions of (E)-17-oxabicyclo[14.1.0]heptadec-8-ene (compounds (1) and (2)) are accessible by synthesis via an epoxidation of a mixture of 1,9-cyclohexadecadiene according to the prior art and subsequent fractional distillation of the epoxide isomers.

The invention furthermore provides the use of (E)-17-oxabicyclo[14.1.0]heptadec-8-ene or of an odoriferous or aroma substance mixture comprising (E)-17-oxabicyclo[14.1.0]heptadec-8-ene (in each case as characterized above) as a musk odoriferous or aroma substance or musk odoriferous or aroma substance mixture, as a fixative and for increasing the olfactory perception of another odoriferous substance.

In a corresponding method according to the invention for imparting, intensifying or modifying a musk smell, a sensorially active amount of (E)-17-oxabicyclo[14.1.0]heptadec-8-ene (compound (1) and/or compound (2)) or an odoriferous or aroma substance mixture according to the invention comprising (E)-17-oxabicyclo[14.1.0]heptadec-8-ene (in each case as characterized above) is brought into contact or mixed with a product.

The invention also relates to perfumed products comprising a solid or semi-solid carrier and a sensorially active amount, in contact with the carrier, of (E)-17-oxabicyclo[14.1.0]heptadec-8-ene or of an odoriferous or aroma substance mixture according to the invention comprising (E)-17-oxabicyclo[14.1.0]heptadec-8-ene (in each case as characterized above).

Conventional other perfume constituents with which (E)-17-oxabicyclo[14.1.0]heptadec-8-ene (1), (E)-17-oxabicyclo[14.1.0]heptadec-8-ene (2) or mixtures thereof can advantageously be combined are to be found e.g. in Steffen Arctander, Perfume and Flavor Chemicals, private publishing house, Montclair, N.J., 1969; K. Bauer, D. Garbe, H. Surburg, Common Fragrance and Flavor Materials, 4th Edition, Wiley-VCH, Weinheim 2001.

There may be mentioned in detail:

extracts from natural raw materials, such as essential oils, concretes, absolutes, resins, resinoids, balsams, tinctures, such as e.g. amber tincture; amyris oil; angelica seed oil; angelica root oil; aniseed oil; valerian oil; basil oil; tree moss absolute; bay oil; artemisia oil; benzoin resin; bergamot oil; beeswax absolute; birch tar oil; bitter almond oil; bean leaf oil; buchu leaf oil; cabreuva oil; cade oil; calamus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiva balsam; copaiva balsam oil; coriander oil; costus root oil; cumin oil; cypress oil; davana oil; dill weed oil; dill seed oil; eau de brouts absolute; oak moss absolute; elemi oil; tarragon oil; Eucalyptus citriodora oil; eucalyptus oil; fennel oil; spruce needle oil; galbanum oil; galbanum resin; geranium oil; grapefruit oil; guaiac wood oil; gurjunene balsam; gurjunene balsam oil; helichrysum absolute; helichrysum oil; ginger oil; iris root absolute; iris root oil; jasmine absolute; calamus oil; camomile oil blue; camomile oil Roman; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon grass oil; lovage oil; lime oil distilled; lime oil pressed; linaloa oil; Litsea cubeba oil; bay leaf oil; mace oil; marjoram oil; mandarin oil; massoi bark oil; mimosa absolute; musk seed oil; musk tincture; muscatel sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; oregano oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rose wood oil; rose oil; rosemary oil; sage oil Dalmatian; sage oil Spanish; sandalwood oil; celery seed oil; spike lavender oil; star aniseed oil; styrax oil; tagetes oil; fir needle oil; tea tree oil; terpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil; and fractions thereof or constituents isolated therefrom;

individual odoriferous substances from the group consisting of the hydrocarbons, such as e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

the aliphatic alcohols, such as e.g. hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; the aliphatic aldehydes and 1,4-dioxacycloalken-2-ones thereof, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyloxyacetaldehyde;

the aliphatic ketones and oximes thereof, such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; the aliphatic sulfur-containing compounds, such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles, such as e.g. 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

the aliphatic carboxylic acids and esters thereof, such as e.g. (E)- and (Z)-3-hexyenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate; methyl 2-nonynate; allyl 2-isoamyloxyacetate; methyl 3,7-dimethyl-2,6-octadienoate;

the acyclic terpene alcohols, such as e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates; 3-methyl-2-butenoates thereof;

the acyclic terpene aldehydes and ketones, such as e.g. geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral; 7-hydroxy-3,7-dimethyloctanal;

the cyclic terpene alcohols, such as e.g. menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol and guaiol; and formates, acetates, propionates, isobutyrates, butyrates, isovalerates, pentanoates, hexanoates, crotonates, tiglinates; 3-methyl-2-butenoates thereof;

the cyclic terpene aldehydes and ketones, such as e.g. menthone; isomenthone; 8-mercaptomenthan-3-one; carvone; camphor; fenchone; alpha-ionone; betaionone; alpha-n-methylionone; beta-n-methylionone; alpha-isomethylionone; beta-isomethylionone; alpha-irone; alpha-damascone; beta-damascone; betadamascenone; deltadamascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alphasinensal; beta-sinensal; acetylated cedar wood oil (methyl cedryl ketone);

the cyclic alcohols, such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols, such as e.g. alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers, such as e.g. cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxane;

the cyclic ketones, such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

the cycloaliphatic aldehydes, such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones, such as e.g. 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols, such as e.g. 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- and -6-indenyl acetate; 4,7-methano-3a,4,5,6,7,7a-hexahydro-5- and -6-indenyl propionate; 4,7-methano-3a,4,5,6,7,7a-hexahydro-5- and -6-indenyl isobutyrate; 4,7-methanooctahydro-5- and 6-indenyl acetate;

the esters of cycloaliphatic carboxylic acids, such as e.g. allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6- dimethyl-2-cyclohexenecarboxylate; ethyl 2,3,6,6-tetramethyl-2-cyclohexenecarboxylate; ethyl 2-methyl-1,3-dioxolane-2-acetate;

the aromatic hydrocarbons, such as e.g. styrene and diphenylmethane;

the araliphatic alcohols, such as e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids, such as e.g.: benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; the araliphatic ethers, such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

the aromatic and araliphatic aldehydes, such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.butylphenyl)propanal; 3-(4-tert.-butylphenyl)propanal; cinnamaldehyde; alphabutylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones, such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof, such as e.g. benzoic acid; phenylacetic acid; methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds, such as e.g. 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl N-methylanthranilate; Schiffs bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

the phenols, phenyl ethers and phenyl esters, such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds, such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones, such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The perfume oils (odoriferous substance mixtures) comprising the mixture according to the invention comprising (E)-17-oxabicyclo[14.1.0]heptadec-8-ene (compound (1) and/or (2)) can be employed for perfuming purposes in liquid form, undiluted or diluted with a solvent. Suitable solvents for this are, in particular, ethanol, isopropanol, diethylene glycol monoethyl ether, glycerol, propylene glycol, 1,2-butylene glycol, dipropylene glycol, diethyl phthalate, triethyl citrate and isopropyl myristate.

For some uses, it is advantageous to employ a perfume oil according to the invention comprising 17-oxabicyclo[14.1.0] heptadec-8-ene which is adsorbed on a carrier substance, which ensures both a fine distribution of the odoriferous substances in the product and a controlled release during use. Such carriers can be porous inorganic materials, such as light sulfate, silica gels, zeolites, cements, gypsums, clays, clay granules, gas concrete and the like, or organic materials, such as woods, cellulose-based substances, sugars or plastics, such as PVC, polyvinyl acetates or polyurethanes.

For other uses, it is advantageous to employ a perfume oil according to the invention comprising 17-oxabicyclo[14.1.0] heptadec-8-ene which is in microencapsulated or spray-dried form or in the form of an inclusion complex or extrusion product and to add it in this form to the precursor/product to be perfumed.

The properties of perfume oils modified in this manner are in some cases optimized further in respect of a more controlled release of fragrance by so-called "coating" with suitable materials, for which purpose waxy plastics, e.g. polyvinyl alcohol, are preferably used.

The microencapsulation of the perfume oils can be carried out, for example, by the co-called coacervation process with the aid of capsule materials e.g. of polyurethane-like substances or soft gelatine. The spray-dried perfume oils can be prepared, for example, by spray drying of an emulsion or dispersion containing the perfume oil, it being possible to use modified starches, proteins, dextrin and plant gums as carrier substances. Inclusion complexes can be prepared e.g. by introducing dispersions of the perfume oil and cyclodextrins or urea derivatives into a suitable solvent, e.g. water. Extrusion products can be achieved by melting the perfume oils with a suitable waxy substance and by extrusion with subsequent solidification, optionally in a suitable solvent, e.g. isopropanol.

The isomer mixtures and odoriferous and aroma substance mixtures according to the invention can be used in concentrated form, in solutions or in an otherwise modified form for the preparation of e.g. perfume extracts, perfume waters, toilet waters, shaving lotions, cologne waters, pre-shave products, splash colognes and perfumed freshening wipes, as well as perfuming of acid, alkaline and neutral cleaning compositions, such as e.g. floor cleaners, window glass cleaners, dishwashing compositions, bath and sanitary cleaners, scouring milk, solid and liquid WC cleaners, powder and foam carpet cleaners, liquid detergents, pulverulent detergents, laundry pretreatment compositions, such as bleaching compositions, soaking compositions and stain removers, laundry softeners, washing soaps, washing tablets, disinfectants, surface disinfectants and air fresheners in liquid or gelatinous form or in a form applied to a solid carrier, aerosol sprays, waxes and polishes, such as furniture polishes, floor waxes, shoe creams as well as body care compositions, such as e.g. solid and liquid soaps, shower gels, shampoos, shaving soaps, shaving foams, bath oils, cosmetic emulsions of the oil-in-water, of the water-in-oil and of the water-in-oil-in-water type, such as e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, such as e.g. hair sprays, hair gels, hair lotions, hair conditioners, permanent and semipermanent hair colouring compositions, hair setting compositions, such as cold waving compositions and hair straightening compositions, hair waters, hair creams and lotions, deodorants and antiperspirants, such as e.g. underarm sprays, roll-ons, deodorant sticks, deodorant creams or products for decorative cosmetics.

In perfume oil compositions, the amount of (E)-17-oxabicyclo[14.1.0]heptadec-8-ene (1) and/or (2) employed is preferably 0.001 to 70 wt. %, particularly preferably 0.05 to 50 wt. % and especially preferably 0.5 to 25 wt. %, based on the total perfume oil composition.

In perfume oil compositions, the amount of 17-oxabicyclo [14.1.0]heptadec-8-ene, that is to say a mixture according to the invention comprising the isomers (1), (2), (3) and (4), employed is preferably 0.01 to 90 wt. %, particularly preferably 0.1 to 70 wt. % and especially preferably 1 to 40 wt. %, based on the total perfume oil composition.

Ingredients with which the isomers can be combined according to the invention are, for example:
preservatives, abrasives, antiacne agents, agents against ageing of the skin, antibacterial agents, anticellulitis agents, antidandruff agents, antiinflammatory agents, irritation-preventing agents, irritation-inhibiting agents, antimicrobial agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, fungicides, gelling agents, gel-forming agents, hair care agents, hair setting agents, hair straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin soothing agents, skin cleansing agents, skin care agents, skin healing agents, skin lightening agents, skin protecting agents, skin softening agents, cooling agents, skin cooling agents, warming agents, skin warming agents, stabilizers, UV-absorbing agents, UV filters, detergents, fabric conditioners, suspending agents, skin tanning agents, thickeners, vitamins, oils, waxes, fats, phospholipids, saturated fatty acids, mono- or polyunsaturated fatty acids, ahydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives.

Further combinations and effects of olfactory interest can be achieved with 17-oxabicyclo[14.1.0]heptadec-8-ene (mixtures or isomers (1) to (4)) in combination with other musk odoriferous substances, in particular musk notes of even richer facets can be created in combination with macrocyclic ketones and, in particular, lactones. Of the lactones, 1,15-cyclopentadecanolide, 11-pentadecen-15-olide, 12-pentadecen-15-olide, 1,16-hexadecanolide and ethylene brassylate or mixtures thereof are preferably to be mentioned. Of the ketones, muscone, muscenone, cyclopentadecanone and cyclohexadecanone are advantageous.

The compounds or mixtures of 17-oxabicyclo[14.1.0]heptadec-8-ene according to the invention and the odoriferous substance or aroma substance mixtures comprising the compounds or mixtures of 17-oxabicyclo[14.1.0]heptadec-8-ene according to the invention (as characterized above) are distinguished by a high absorption capacity (intrinsic adhesion to a substrate) and a high substantivity (ability to be absorbed out of a usually aqueous phase on to a substrate and to remain on a substrate even after a washing or rinsing operation). This effect manifests itself in particular on substrates such as skin, hair and textile fibres (e.g. wool, cotton, linen, synthetic fibres).

Particularly preferred perfumed products according to the invention are therefore detergents and hygiene or care products, in particular in the field of body care, cosmetics and household products.

In addition, odoriferous substances which improve the adhesiveness of the composition (that is to say act as fixatives) or increase the intensity of the olfactory perception (that is to say function as boosters) are of great interest.

In addition to a high absorption capacity, (E)-17-oxabicyclo[14.1.0]heptadec-8-ene and the mixtures according to the invention are distinguished by their fixing properties. Such a fixative increases the adhesiveness of other odoriferous substances, either by their lowering of vapour pressure or olfactory intensification (e.g. lowering of the threshold value). The invention therefore also relates to the use of 17-oxabicyclo [14.1.0]heptadec-8-ene or an odoriferous substance or aroma substance mixture comprising 17-oxabicyclo[14.1.0]heptadec-8-ene (as characterized above) as a fixative.

17-Oxabicyclo[14.1.0]heptadec-8-ene and the mixtures according to the invention furthermore act not only as fixatives but also as so-called boosters or enhancers, i.e. they have the effect of intensifying the smell or the olfactory perception of odoriferous substances, odoriferous substance mixtures and perfume compositions. The invention therefore also relates to the use of 17-oxabicyclo[14.1.0]heptadec-8-ene or an odoriferous substance mixture comprising 17-oxabicyclo[14.1.0]heptadec-8-ene (as characterized above) as agents for increasing the olfactory perception of odoriferous substances or odoriferous substance compositions.

The influences described for the isomers of 17-oxabicyclo[14.1.0]heptadec-8-ene and the mixtures according to the invention on odoriferous substance compositions manifest themselves in particular by comparison of the olfactory change with respect to time during use.

The following examples illustrate the invention; unless stated otherwise, contents and percentages relate to the weight.

EXAMPLE 1

Preparation of 17-oxabicyclo[14.1.0]heptadec-8-ene/Determination of the Conversion Factors 10 g 1,9-cyclohexadecadiene of the following composition are added to a solution of 14.1 g sodium acetate in 75 ml methylene chloride and the mixture is cooled to 0° C.: (Z,Z)-1,9-cyclohexadecadiene 18%, (E,Z)-1,9-cyclohexadecadiene 54%, (E,E)-1,9-cyclohexadecadiene 28%. 8.6 g peracetic acid (40% strength) in 15 ml methylene chloride are slowly added dropwise at this temperature and the mixture is subsequently stirred for three hours at 0° C. The reaction solution is poured on to ice-water and extracted once with methylene chloride. The combined organic phases are washed with saturated NaCl solution and subsequently dried with magnesium sulfate, and after removal of the solvent 9.0 g of crude product are obtained. After purification by chromatography with ethyl acetate/cyclohexane, a product having the following composition is obtained: (E)-17-oxabicyclo[14.1.0]heptadec-8-ene (1) 33%, (E)-17-oxabicyclo[14.1.0]heptadec-8-ene (2) 28%, (Z)-17-oxabicyclo[14.1.0]heptadec-8-ene (3) 21%, (Z)-17-oxabicyclo[14.1.0]heptadec-8-ene (4) 18%.

The following conversion factors result from this for the individual isomers: epoxides (2) and (4) are each formed with the factor 1. Compound (3) reacts with a conversion factor of 0.78 and epoxide (1) is formed with a factor of 1.22.

(E)-17-Oxabicyclo[14.1.0]heptadec-8-ene (1)

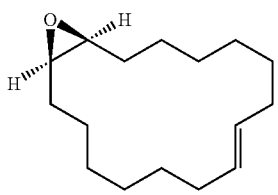

1

$^1$H-NMR (400 MHz, CDCl$_3$): δ=1.16-1.45 (m, 16 H), 1.54-1.70 (m, 4 H), 1.98-2.10 (m, 4 H), 2.87-2.92 (m, 2 H), 5.24-5.33 (m, 2 H) ppm.
$^{13}$C-NMR (100 MHz, CDCl$_3$): δ=25.59 (CH$_2$), 26.50 (CH$_2$), 27.17 (CH$_2$), 28.29 (CH$_2$), 28.57 (CH$_2$), 32.17 (CH$_2$), 56.92 (CH), 131.09 (CH) ppm.
MS: m/z (%)=236 (3) [M$^+$], 189 (1), 161 (4), 147 (5), 135 (11), 121 (16), 109 (17), 95 (43), 81 (71), 67 (100), 55 (89), 41 (96).
IR: 1/λ=805 (w), 973 (m, trans-DB), 1461 (m), 2854 (vs), 2926 (vs), 2959 (s), 3030 (w) cm$^{-1}$.

(E)-17-Oxabicyclo[14.1.0]heptadec-8-ene (2)

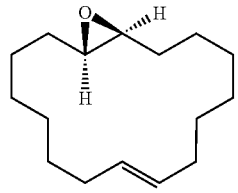

2

$^1$H-NMR (400 MHz, CDCl$_3$): δ=1.16-1.64 (m, 18 H), 1.75-1.86 (m, 2 H), 1.95-2.10 (m, 4 H), 2.64-2.69 (m, 2 H), 5.38-5.42 (m, 2 H) ppm.
$^{13}$C-NMR (100 MHz, CDCl$_3$): δ=26.20 (CH$_2$), 26.50 (CH$_2$), 28.50 (CH$_2$), 29.90 (CH$_2$), 30.15 (CH$_2$), 30.91 (CH$_2$), 58.80 (CH), 130.70 (CH) ppm.
MS: m/z (%)=236 (2) [M$^+$], 175 (2), 165 (3), 161 (4), 151 (3), 147 (5), 135 (11), 121 (17), 112 (11), 109 (18), 95 (45), 81 (72), 67 (100), 55 (88), 41 (92).
IR: 1/λ=745 (w), 875 (w), 972 (m, trans-DB), 1353 (w), 1446 (m), 1462 (m), 2853 (s), 2925 (vs), 2981 (m), 3031 (w) cm$^{-1}$.

(Z)-17-Oxabicyclo[14.1.0]heptadec-8-ene (3)

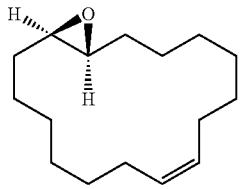

3

$^1$H-NMR (400 MHz, CDCl$_3$): δ=1.20-1.56 (m, 18 H), 1.94-2.12 (m, 6 H), 2.64-2.68 (m, 2 H), 5.35-5.42 (m, 2 H) ppm.
$^{13}$C-NMR (100 MHz, CDCl$_3$): δ=25.61 (CH$_2$), 25.91 (CH$_2$), 27.96 (CH$_2$), 28.08 (CH$_2$), 28.83 (CH$_2$), 31.91 (CH$_2$), 59.71 (CH), 129.95 (CH) ppm.
MS: m/z (%)=236 (2) [M$^+$], 189 (1), 175 (2), 161 (3), 147 (5), 135 (10), 121 (17), 112 (13), 109 (19), 95 (45), 81 (73), 67 (100), 55 (87), 41 (86).
IR: 1/λ=717 (w, cis-DB), 900 (w), 944 (w), 1447 (m), 1466 (m), 2855 (vs), 2926 (vs), 2999 (m) cm$^{-1}$.

(Z)-17-Oxabicyclo[14.1.0]heptadec-8-ene (4)

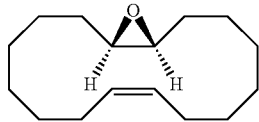

4

$^1$H-NMR (400 MHz, CDCl$_3$): δ=1.22-1.45 (m, 16 H), 1.46-1.55 (m, 2 H), 1.74-1.93 (m, 4 H), 2.14-2.24 (m, 2 H), 2.89-2.94 (m, 2 H), 5.30-5.38 (m, 2 H) ppm.

$^{13}$C-NMR (100 MHz, CDCl$_3$): δ=25.21 (CH$_2$), 26.63 (CH$_2$), 26.84 (CH$_2$), 27.99 (CH$_2$), 28.48 (CH$_2$), 28.75 (CH$_2$), 57.12 (CH), 130.02 (CH) ppm.

MS: m/z (%)=236 (2) [M$^+$], 179 (1), 175 (2), 165 (3), 152 (2), 147 (4), 135 (10), 121 (16), 112 (14), 109 (17), 95 (44), 81 (71), 67 (100), 55 (90), 41 (90).

IR: 1/λ=718 (w, cis-DB), 784 (w), 818 (w), 1000 (w), 1451 (m), 1470 (m), 2854 (vs), 2925 (vs), 2998 (s) cm$^{-1}$.

EXAMPLE 2

Perfume oil (Odoriferous Substance Mixture)

The following base perfume oil serves in practice as a warm sensual male note from the fine fragrance area.

Composition:

| Ingredients | Parts by weight |
|---|---|
| 1. ALDEHYDE C18 SOG. 10% in DPG<br>5-Pentyl-2[3H]-dihydrofuranone | 5 |
| 2. AMBROXIDE CRYSTALLINE<br>Dodecahydro-3a,6,6,9a-tetramethylnaphtho-[2,1-b]furan | 5 |
| 3. BENZYL ACETATE | 10 |
| 4. BENZYL SALICYLATE | 60 |
| 5. CITRONELLOL | 10 |
| 6. COUMARONE 2-Acetyl-benzofuran | 5 |
| 7. DIHYDROMYRCENOL | 20 |
| 8. ETHYLLINALOOL | 40 |
| 9. FLOROSA<br>4-Methyl-2-(2-methylpropyl)-tetrahydro-2H-4-pyranol | 60 |
| 10. FRAMBINONE<br>4-(4-Hydroxyphenyl)-2-butanone | 5 |
| 11. HEDIONE<br>3-Oxo-2-pentyl-cyclopentane-acetic acid methyl ester | 220 |
| 12. HELIONAL<br>alpha-Methyl-3,4-methylenedioxy-hydrocinnamaldehyde | 30 |
| 13. HELIOTROPIN/PIPERONAL 10% in DPG<br>3,4-Methylenedioxybenzaldehyde | 20 |
| 14. HEXENYL SALICYLATE CIS-3 | 40 |
| 15. INDOLE, 1% in DPG | 10 |
| 16. IRON ALPHA 10% in DPG<br>4-(2,5,6,6-Tetramethyl-2-cyclohexen-1-yl)-3-buten-2-one | 10 |
| 17. ISO E SUPER<br>2,3,8,8-Tetramethyl-1,2,3,4,5,6,7,8-octahydro-2-naphthalenyl methyl ketone | 90 |
| 18. ISORALDEINE 95<br>4-(2,6,6-Trimethyl-2-cyclohexen-1-yl)-3-methyl-3-buten-2-one | 30 |
| 19. JASMINE ABS. IND. 1% in DPG | 10 |
| 20. JASMONE CIS 10% DPG<br>cis-3-Methyl-2-(2-pentenyl)-2-cyclopenten-1-one | 5 |
| 21. LILIAL<br>2-Methyl-3-(4-tert-butylphenyl)-propanal | 60 |
| 22. LINALOOL | 40 |
| 23. MAGNOLIA BLOSSOM OIL 10% in DPG | 5 |
| 24. MANDARIN OIL DIST. COLOURLESS | 20 |
| 25. PARMANYL ® 10% in DPG<br>3-(cis-Hexenyloxy)-propanenitrile | 10 |
| 26. SANDALWOOD 80<br>trans-3-Isocamphylcyclohexanol | 20 |
| 27. SANDRANOL ®<br>2-Ethyl-4-(2,2,3-trimethyl-3-cyclopenten-1-yl)-2-buten-1-ol | 40 |
| 28. VANILLIN | 5 |
| 29. VERTOCITRAL 10% in DPG<br>2,4-Dimethyl-3-cyclohexenecarboxaldehyde | 5 |
| 30. YLANG YLANG OIL EXTRA FF 10% in DPG | 20 |
| 31. YSAMBER ® K<br>Hexahydro-1',1',5',5'-tetramethyl-spiro[1,3-dioxolane-2,8'(5'H)-[2H-2,4a]-methano-naphthalene | 10 |
| TOTAL | 920 |

DPG = dipropylene glycol

The addition of 80 parts by weight of (E)-17-oxabicyclo[14.1.0]heptadec-8-ene (1) (total of base perfume oil employed: 1,000 parts by weight) led to a significantly perceptible harmonizing of the overall composition. The perfume oil has a more radiant and powdery effect with a woody-ambered background. (E)-17-Oxabicyclo[14.1.0]heptadec-8-ene (1) combines the flowery heart with the sensual background of the note. Furthermore, the addition of (E)-17-oxabicyclo[14.1.0]heptadec-8-ene (1) had the effect of erogenous, crystalline, elegant, exalting and natural musk notes in the overall composition. In this context, the valuable character of (E)-17-oxabicyclo[14.1.0]heptadec-8-ene (1) compared with compositions with conventional macrocyclic musk odoriferous substances asserted itself in particular. (E)-17-Oxabicyclo[14.1.0]heptadec-8-ene (1) imparted to the present composition an outstanding radiance and increased adhesion.

EXAMPLE 3

Washing Powder

The perfume composition from Example 2 (after addition of 2-methoxymethylphenol) was incorporated in a dosage of 0.3 wt. % into a washing powder base composition of the following recipe:

| | |
|---|---|
| Linear Na alkylbenzenesulfonate | 8.8% |
| Ethoxylated fatty alcohol C12-18 (7 EO) | 4.7% |
| Na soap | 3.2% |
| Defoamer<br>DOW CORNING(R) 2-4248S<br>POWDERED ANTIFOAM | |
| Silicone oil on zeolite as a carrier material | 3.9% |
| Zeolite 4A | 28.3% |
| Na carbonate | 11.6% |
| Na salt of a copolymer of acrylic and maleic acid (Sokalan CP5) | 2.4% |
| Na silicate | 3.0% |
| Carboxymethylcellulose | 1.2% |
| Dequest 2066<br>([[[(Phosphonomethyl)imino]bis[(ethylenenitrilo)bis-(methylene)]]tetrakis-phosphonic acid, sodium salt) | 2.8% |
| Optical brightener | 0.2% |
| Na sulfate | 6.5% |
| Protease | 0.4% |
| Sodium perborate tetrahydrate | 1.7% |
| Odoriferous substance composition having a rose smell | 0.3% |
| TAED | 1.0% |

Two fabric rags were washed with 370 g of a 1% strength aqueous washing powder liquor (the pH of the washing powder liquor was significantly in the basic range) in a Linetest machine in the main wash cycle for 45 minutes at 60° C. The rags were first rinsed with cold water for 5 minutes, wrung out and then spun for 20 seconds. One rag was sealed while wet, and one was hung up to dry. The olfactory properties of the two rags were then evaluated by a panel. Both rags displayed a flowery, powdery, woody-ambered smell with erogenous, crystalline, elegant, exalting and natural musk notes, the overall impression being perceived as radiant, rounded and harmonious.

EXAMPLE 4

Shampoo

2-Methoxymethylphenol was provided as a 50 wt. % strength solution in diethyl phthalate, which was incorporated in a dosage of 0.2 wt. % into a shampoo base composition of the following recipe:

| | |
|---|---|
| Sodium lauryl ether-sulfate (e.g. Texapon NSO, Cognis Deutschland GmbH) | 12% |
| Cocamidopropylbetaine (e.g. Dehyton K, Cognis Deutschland GmbH) | 2% |
| Sodium chloride | 1.4% |
| Citric acid | 1.3% |
| Phenoxyethanol, methyl-, ethyl-, butyl- and propylparaben | 0.5% |
| Peach odoriferous substance mixture comprising gamma-undecalactone | 0.5% |
| Water | 82.3% |

The pH of the shampoo base composition was about 6, 100 ml of a 20 wt. % strength aqueous shampoo solution were prepared from this. 2 hanks of hair were washed together in this shampoo solution for 2 minutes and were then rinsed for 20 seconds under running hand-hot water. One hank of hair was packed in aluminium foil while wet and the second hank of hair was dried with a hair-dryer. The olfactory properties of the two hanks of hair were evaluated by a panel. Both hanks of hair displayed a flowery, powdery, woody-ambered smell with erogenous, crystalline, elegant, exalting and natural musk notes, the overall impression being perceived as radiant, rounded and harmonious.

SPECIFIC EMBODIMENTS

Specific embodiment one comprises an isomer mixture of isomers of 17-oxabicyclo[14.1.0]heptadec-8-ene, having a content of an (E)-17-oxabicyclo[14.1.0]heptadec-8-ene isomer (1) and/or (2), characterized in that
a) if the isomer mixture contains four isomers (1), (2), (3) and (4), the content of isomer (1) is greater than 32 wt. % and/or the content of isomer (2) is greater than 12 wt. %,
b) if the isomer mixture contains only two or three isomers chosen from the isomers (1), (2), (3) and (4), the content of isomer (1) and/or isomer (2) is at least 45 wt. %, in each case based on the total weight of the isomer mixture.

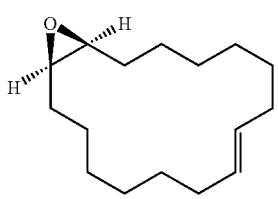

1

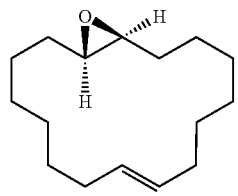

2

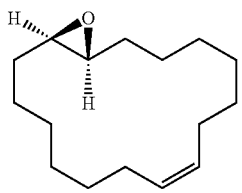

3

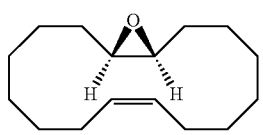

4

Specific embodiment two comprises an isomer mixture according to specific embodiment one, characterized in that the content of (E)-17-oxabicyclo[14.1.0]heptadec-8-ene (1) is greater than 32 wt. %, based on the total weight of the isomer mixture.

Specific embodiment three comprises an isomer mixture according to one of specific embodiments one or two, characterized in that the content of (E)-17-oxabicyclo[14.1.0]heptadec-8-ene (1) is at least 40 wt. %, based on the total weight of the isomer mixture.

Specific embodiment four comprises an isomer mixture according to one of the preceding specific embodiments, characterized in that it has a content of (E)-17-oxabicyclo[14.1.0]heptadec-8-ene (1) of at least 50 wt. %.

Specific embodiment five comprises an isomer mixture according to one of the preceding specific embodiments, having a content of at least 25 wt. % of (E)-17-oxabicyclo[14.1.0]heptadec-8-ene (2), based on the total weight of the isomer mixture.

Specific embodiment six comprises an isomer mixture according to one of the preceding specific embodiments, characterized in that the content of isomers (1) and (2) ((E) double bond content)

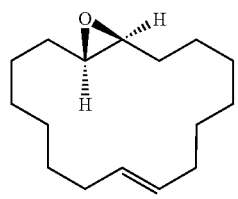

2 in total is greater than 45 wt. %, based on the total weight of the isomer mixture.

Specific embodiment seven comprises an isomer mixture according to one of the preceding specific embodiments, characterized in that it has an (E) double bond content of at least 55 wt. %.

Specific embodiment eight comprises an isomer mixture according to one of the preceding specific embodiments, characterized in that it has an (E) double bond content of at least 60 wt. %.

Specific embodiment nine comprises an odoriferous or aroma substance mixture, comprising an isomer mixture of 17-oxabicyclo[14.1.0]heptadec-8-ene according to one of specific embodiments one to eight and one or more further odoriferous or aroma substances.

Specific embodiment ten comprises a perfumed product, comprising a solid or semi-solid carrier and a sensorially active amount, in contact with the carrier or mixed with it, of an isomer mixture according to one of specific embodiments one to eight or of an odoriferous or aroma substance mixture according to specific embodiment nine.

Specific embodiment eleven comprises a perfumed product according to specific embodiment ten, wherein the product is a detergent or a hygiene or care product.

Specific embodiment twelve comprises an isomer mixture according to one of specific embodiments one to eight or of an odoriferous or aroma substance mixture according to specific embodiment nine for imparting, intensifying and/or modifying a musk smell or aroma.

Specific embodiment thirteen comprises a method of imparting, intensifying or modifying a musk smell, having the following step:

bringing into contact or mixing of a sensorially active amount of an isomer mixture according to one of specific embodiments one to eight or of an odoriferous or aroma substance mixture according to specific embodiment nine with a product.

Specific embodiment fourteen comprises a use of 17-oxabicyclo[14.1.0]heptadec-8-ene (1) and/or (2), of an isomer mixture according to one of specific embodiments one to eight or of an odoriferous or aroma substance mixture according to specific embodiment nine comprising an (E)-17-oxabicyclo[14.1.0]heptadec-8-ene as a fixative.

Specific embodiment fifteen comprises a use of 17-oxabicyclo[14.1.0]heptadec-8-ene (1) and/or (2) or of an odoriferous substance mixture according to specific embodiment nine comprising an (E)-17-oxabicyclo[14.1.0]heptadec-8-ene as an agent for increasing the olfactory perception of other odoriferous substances or odoriferous substance compositions.

It is claimed:

1. A composition comprising a mixture of isomers of 17-oxabicyclo[14.1.0]heptadec-8-ene, having a content of an (E)-17-oxabicyclo[14.1.0]heptadec-8-ene isomer (1) and/or (2),

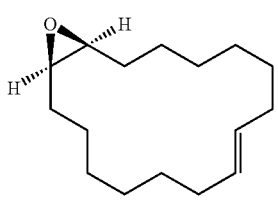
1

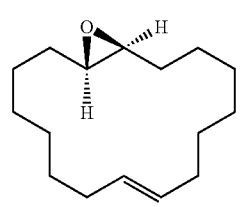
2

-continued

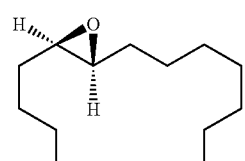
3

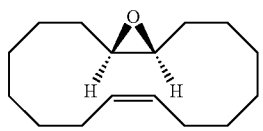
4 wherein
a) if the isomer mixture contains four isomers (1), (2), (3) and (4), the content of isomer (1) is greater than 32 wt. % and/or the content of isomer (2) is greater than 12 wt. %,
b) if the isomer mixture contains only two or three isomers chosen from the isomers (1), (2), (3) and (4), the content of isomer (1) and/or isomer (2) is at least 45 wt. %,
in each case based on the total weight of the isomer mixture.

2. The composition according to claim 1, wherein the content of (E)-17-oxabicyclo[14.1.0]heptadec-8-ene (1) is greater than 32 wt. %, based on the total weight of the isomer mixture.

3. The composition according to claim 1, wherein the content of (E)-17-oxabicyclo[14.1.0]heptadec-8-ene (1) is at least 40 wt. %, based on the total weight of the isomer mixture.

4. The composition according to claim 1, wherein the composition has a content of (E)-17-oxabicyclo[14.1.0]heptadec-8-ene (1) of at least 50 wt. %.

5. The composition according to claim 1, wherein the content of (E)-17-oxabicyclo[14.1.0]heptadec-8-ene (2) is at least 25 wt. % based on the total weight of the isomer mixture.

6. The composition according to claim 1, wherein the content of isomers (1) and (2) ((E) double bond content)

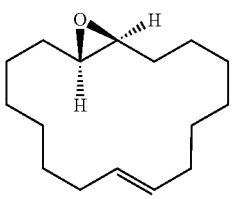
2 in total is greater than 45 wt. %, based on the total weight of the isomer mixture.

7. The composition according to claim 1, wherein the (E) double bond content is at least 55 wt. %.

8. The composition according to claim 1, wherein the content of (E) double bond content is at least 60 wt. %.

9. A composition comprising an odoriferous or aroma substance mixture, comprising an isomer mixture of 17-oxabicyclo[14.1.0]heptadec-8-ene according to claim 1 and one or more further odoriferous or aroma substances.

10. A composition comprising a perfumed product, comprising a solid or semi-solid carrier and a sensorially active amount, in contact with the carrier or mixed with it, of an odoriferous or aroma substance mixture according to claim 9.

11. A composition comprising a perfumed product according to claim 10, wherein the product is a detergent or a hygiene or care product.

12. A method for imparting, intensifying and/or modifying a musk smell or aroma comprising employing an odoriferous or aroma substance mixture according to claim 9 in a solid carrier, aerosol spray, wax, polish, or body care composition.

13. A method of imparting, intensifying or modifying a musk smell, having the following step:
bringing into contact or mixing with a product, a sensorially active amount of an odoriferous or aroma substance mixture according to claim 9.

14. A composition comprising a perfumed product, comprising a solid or semi-solid carrier and a sensorially active amount, in contact with the carrier or mixed with it, of an isomer mixture according to claim 1.

15. A composition comprising a perfumed product according to claim 14, wherein the product is a detergent or a hygiene or care product.

16. A method for imparting, intensifying and/or modifying a musk smell or aroma comprising employing the composition of an isomer mixture according to claim 1 in a solid carrier, aerosol spray, wax, polish, or body care composition.

17. A method of imparting, intensifying or modifying a musk smell, having the following step:
bringing into contact or mixing a product with a sensorially active amount of an isomer mixture according to claim 1.

18. A fixative comprising
an isomer mixture of 17-oxabicyclo[14.1.0]heptadec-8-ene (1) and/or (2) according to claim 1.

19. An agent for increasing the olfactory perception of other odoriferous substances or odoriferous substance compositions comprising an isomer mixture of 17-oxabicyclo[14.1.0]heptadec-8-ene (1) and/or (2) or of an odoriferous substance mixture according to claim 9.

* * * * *